United States Patent
Muggleton

(10) Patent No.: US 10,744,038 B2
(45) Date of Patent: Aug. 18, 2020

(54) USE OF HEARING PROTECTION TO DISCRIMINATE BETWEEN DIFFERENT AND IDENTIFY INDIVIDUAL NOISE SOURCES TO CONTROL AND REDUCE RISK OF NOISE INDUCED HEARING LOSS

(71) Applicant: Honeywell International Inc., Morris Plains, NJ (US)

(72) Inventor: Neal Muggleton, Stevenage (GB)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 68 days.

(21) Appl. No.: 15/998,880

(22) Filed: Aug. 16, 2018

(65) Prior Publication Data
US 2019/0053950 A1 Feb. 21, 2019

Related U.S. Application Data

(60) Provisional application No. 62/546,089, filed on Aug. 16, 2017.

(51) Int. Cl.
*A61F 11/14* (2006.01)
*G10K 11/175* (2006.01)
*G08B 21/02* (2006.01)
*H04R 1/10* (2006.01)

(52) U.S. Cl.
CPC .............. *A61F 11/14* (2013.01); *G08B 21/02* (2013.01); *G10K 11/175* (2013.01); *H04R 1/1083* (2013.01); *A61F 2011/145* (2013.01)

(58) Field of Classification Search
CPC .... A61F 11/06; A61F 11/14; A61F 2011/145; G08B 21/02; G10K 11/175; H04R 1/1083

USPC ..................................................... 381/72, 56
See application file for complete search history.

(56) References Cited

U.S. PATENT DOCUMENTS

| 2010/0142715 | A1* | 6/2010 | Goldstein | G06F 16/686 |
| | | | | 381/56 |
| 2012/0321094 | A1 | 12/2012 | Schiller et al. | |
| 2016/0076858 | A1* | 3/2016 | Howes | A61F 11/06 |
| | | | | 273/371 |

(Continued)

FOREIGN PATENT DOCUMENTS

CN 104581494 A 4/2015

OTHER PUBLICATIONS

Europe Patent Application No. 18189288.6, Extended European Search Report, dated Dec. 19, 2018, 9 pages.

(Continued)

*Primary Examiner* — Harry S Hong
(74) *Attorney, Agent, or Firm* — Alston & Bird LLP

(57) ABSTRACT

Embodiments relate generally to devices, systems, and methods for monitoring sounds. A method may comprise monitoring environmental sounds with a hearing protection device; transmitting acoustic signatures from the hearing protection device to a portable electronic device; transmitting the acoustic signatures from the portable electronic device to a server; correlating the acoustic signatures with information in a database; transmitting a message from the server to the portable electronic device indicating the correlation; creating a suggestion with the portable electronic device based on the correlation; and transmitting the suggestion from the portable electronic device to the hearing protection device based on the correlation.

17 Claims, 1 Drawing Sheet

(56) References Cited

U.S. PATENT DOCUMENTS

| | | |
|---|---|---|
| 2016/0078568 A1 | 3/2016 | Howes |
| 2016/0150333 A1 | 5/2016 | Goldstein et al. |
| 2019/0083320 A1* | 3/2019 | Gustavsson ............ A61F 11/14 |

OTHER PUBLICATIONS

Intention to Grant for European Patent Application No. 18189288.6 dated Mar. 18, 2020, 5 pages.

* cited by examiner

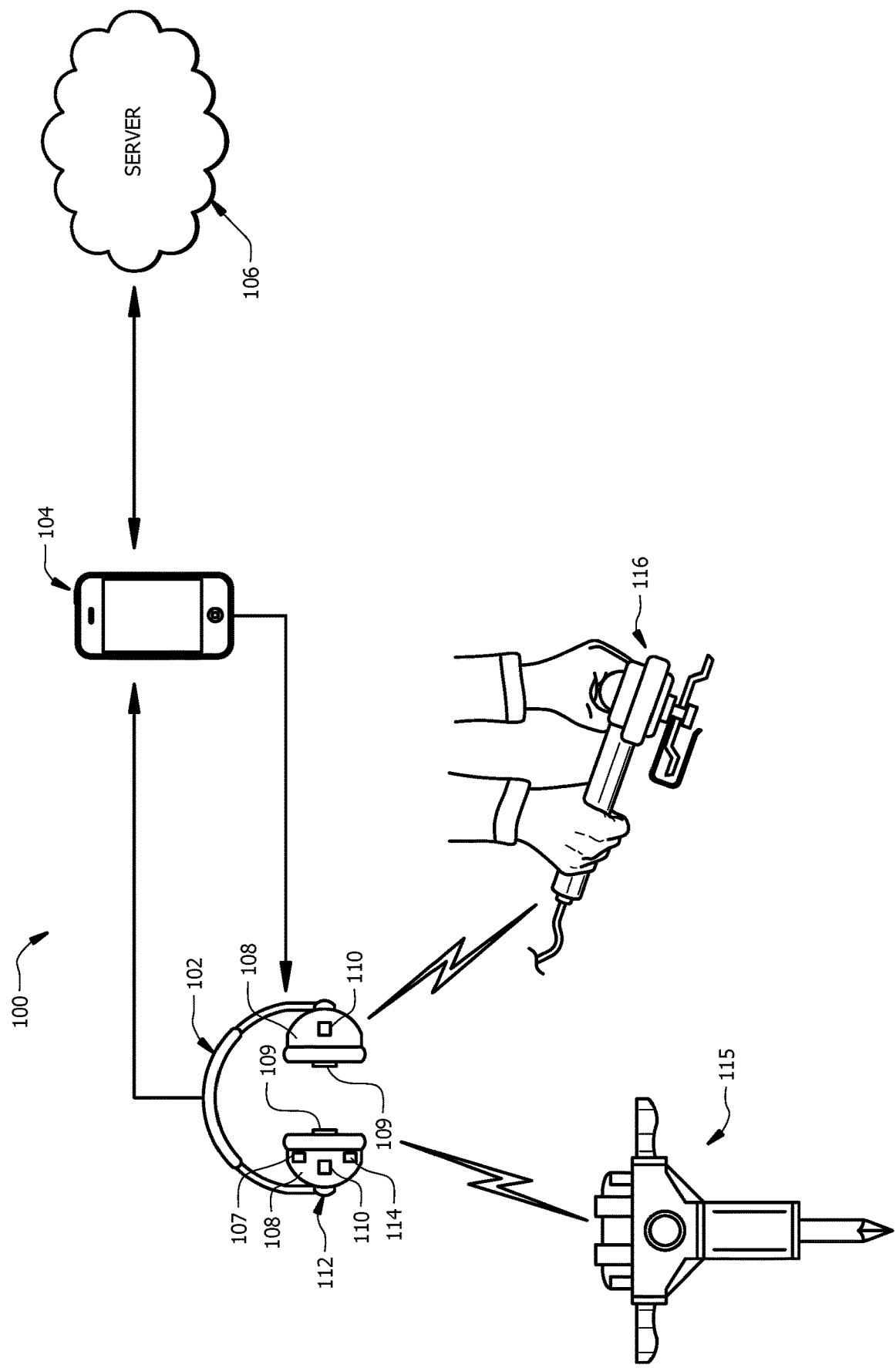

USE OF HEARING PROTECTION TO DISCRIMINATE BETWEEN DIFFERENT AND IDENTIFY INDIVIDUAL NOISE SOURCES TO CONTROL AND REDUCE RISK OF NOISE INDUCED HEARING LOSS

CROSS-REFERENCE TO RELATED APPLICATIONS

The present application claims priority to U.S. Provisional Patent Application Ser. No. 62/546,089 filed Aug. 16, 2017 by Neal Muggleton and entitled "Use of Hearing Protection to Discriminate between Different Noises and Identify Individual Noise Sources to Control and Reduce Risk of Noise Induced Hearing Loss" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Some environments are noisy due to industrial equipment. The noise from this equipment can cause permanent hearing damage to workers if protection is not provided. To reduce the noise level in these types of environments to a safe level, hearing protection devices ("HPDs"), such as, for example, ear muffs or ear plugs may be utilized.

SUMMARY

In an embodiment, a system may comprise: a hearing protection device; a server; and a portable electronic device; wherein the server is wirelessly coupled to the portable electronic device; wherein the portable electronic device is wirelessly coupled to the hearing protection device.

In an embodiment, a method may comprise monitoring environmental sounds with a hearing protection device; transmitting acoustic signatures from the hearing protection device to a portable electronic device; transmitting the acoustic signatures from the portable electronic device to a server; correlating the acoustic signatures with information in a database; transmitting a message from the server to the portable electronic device indicating the correlation; creating a suggestion with the portable electronic device based on the correlation; and transmitting the suggestion from the portable electronic device to the hearing protection device based on the correlation.

In an embodiment, a system may comprise a hearing protection device configured to monitor sounds in an industrial environment and transmit acoustic signatures to a portable electronic device; wherein the portable electronic device is configured to transmit the acoustic signatures to a server; wherein the server is configured to correlate the acoustic signatures with information in a database and transmit a message to the portable electronic device indicating the correlation; wherein the portable electronic device is further configured to create and transmit a suggestion to the hearing protection device based on the correlation.

These and other features will be more clearly understood from the following detailed description taken in conjunction with the accompanying drawings and claims.

BRIEF DESCRIPTION OF THE DRAWING

For a more complete understanding of the present disclosure, reference is now made to the following brief description, taken in connection with the accompanying drawings and detailed description, wherein like reference numerals represent like parts.

FIG. 1 is a schematic illustration of a system for monitoring environmental sounds in accordance with embodiments of the disclosure.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example ±10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Current noise assessment and measurement solutions generally only consider the intensity and duration of noise/sound to calculate the continuous average or instantaneous peak noise exposure as defined in global regulations. This limited data may impact the effectiveness of post event analysis to determine a root cause and identify corrective actions to drive better Hearing Conservation policy, procedures, and protective equipment.

Within industrial settings, a significant contributor to the noise landscape may be hand, portable, and semi-portable tools/equipment that may be used as part of operations, either full or part-time. Frequently, these tools and equipment may not be present during the noise risk assessment, and so may not be considered in an effective way in the Hearing Conservation planning.

In current cases where organizations have identified the need to better understand the contributing noise sources to the noise landscape, users may be required to manually identify and record the tools/equipment that either they or co-workers, working in their close proximity are operating. These organizations may also undertake discrete studies of the tools/equipment used across their operations so that they can define policies on their use, including additional training and limitations on the use of the studied equipment. In some cases, these studies may form the basis of improvement efforts to modify the equipment to reduce the noise output or form the basis of equipment replacement programs to purchase new, quieter equipment. These current processes may be time-consuming to administer, and therefore, they may have limited effectiveness at controlling the extent that these tools/equipment impact an overall noise exposure for workers.

Embodiments of the disclosure may relate to a headset (e.g., a hearing protection device that may be in-ear or over-ear) that monitors environmental sounds (e.g., industrial environments). The headset may process sound/noise to identify patterns of sounds associated with industrial equipment (e.g., hand tools, portable equipment, etc.). This processed sound may be shared with a connected system (e.g., a wireless network) to calculate key information for the equipment.

Embodiments of the disclosure may be configured to determine if the tool/equipment is being used optimally, and identify if the tool/equipment is excessively increasing individual noise exposure and advise user to limit/stop using the tool/equipment, thereby extending a safe working time. Embodiments of the disclosure may be configured to monitor the tool/equipment and identify if a tool/equipment requires maintenance or replacement. Embodiments of the disclosure may be configured to determine a contribution a specific tool/equipment is making to a worker's exposure profile, where the worker may be given guidance to stop using a tool/equipment or change tool/equipment so that the worker can limit his/her exposure. Embodiments of the disclosure may be configured to allow co-workers (e.g., people in close proximity to the tool/equipment, but not using the tool/equipment) to determine that their exposure is being affected by a tool/equipment, where guidance may be given to take avoiding action. Embodiments of the disclosure may be configured to, at the end of a work shift, give an overview of the factors/elements contributing to how the exposure was created for each individual, which may be accomplished through an app or a web portal (e.g., it was determined that 25% of noise exposure was from hand tool X, embodiments could recommend that hand tool X is changed or the time used is limited to a number of hours). Embodiments of the disclosure may be configured to advise the worker when the time limit is reached for using a specific tool/equipment in the future (e.g., based on previously collected exposure data for that tool/equipment) via messages through the headset and/or via an app. In other words, embodiments of the disclosure may go beyond the 'exposure measurement' and 'dose time calculation remaining' and actively manage the use of key noise sources that impact an individual's exposure.

FIG. 1 is a schematic illustration of system 100 for monitoring environmental sounds. System 100 may include hearing protection device ("HPD") 102, portable electronic device 104 (e.g., a smart phone), and server 106 (e.g., a cloud based server). Portable electronic device 104 and server 106 may each include a transceiver for communication. HPD 102 may be wirelessly coupled to portable electronic device 104, and server 106 may be wirelessly coupled to portable electronic device 104. Server 106 and portable electronic device 104 may communicate with each other. HPD 102 and portable electronic device 104 may communicate with each other.

HPD 102 may include a processing system 107 (e.g., memory and processor) and include ear cups 108. Each ear cup 108 may include externally facing microphone 110. At least one ear cup 108 may include an externally facing button 112 for a user interface/confirmation, and transceiver 114. In certain embodiments, HPD 102 may include earbuds (with externally facing microphones) which may be inserted into an ear canal. HPD 102 may monitor sounds of the environment through microphones 110. HPD 102 may perform acoustic processing/pattern recognition on the sound monitored via processing system 107. The sounds monitored may be sourced from equipment/tools, such as, for example, jack hammer 115 and angle grinder 116. Each tool or piece of equipment may emit a specific acoustic signature. The acoustic signatures may be monitored/received by HPD 102 and then transmitted (e.g., via transceiver 114) to portable electronic device 104. Once the acoustic signatures are received at portable electronic device 104, portable electronic device 104 may transmit the acoustic signatures to server 106 for analysis. Server 106 may include a database that may include information, such as, for example: a list of users; an equipment/tool library (e.g., listing of types of equipment/tools); acoustic signatures of sounds emitted from various pieces of equipment/tools; equipment/tool usage details (e.g., time spent using tool (duration), application (how the tool/equipment is being utilized), etc.); and/or equipment/tool health (e.g., measured in decibels ("dB"): if the equipment/tool is not functioning properly, the sound it creates may be outside of a properly functioning decibel range/limit and/or acoustic signature range/limit which would indicate an unhealthy/improperly operating tool/equipment)).

The information in the database may have been submitted/stored to/in the database prior to the transmission of the acoustic signatures to server 106 by portable electronic device 104. Table 1 is an example of tabulated information in the database: a list of users; an equipment/tool library (e.g., tool type); acoustic signatures of sounds emitted from each piece of equipment/tool; equipment/tool usage details; and equipment/tool health.

TABLE 1

User; Tool Type; Acoustic Signature; Tool Usage Details; Tool Health

| User | Equipment/Tool Type | Acoustic Pattern of Sound Emitted from Equipment/Tool | Equipment/Tool Usage Details | Equipment/Tool Health |
|---|---|---|---|---|
| User 1 | Tool A (e.g., jack hammer) | Acoustic Signature X | e.g., hammering for 2 hours | Noise level (e.g., 100 dB) |

TABLE 1-continued

User; Tool Type; Acoustic Signature; Tool Usage Details; Tool Health

| User | Equipment/Tool Type | Acoustic Pattern of Sound Emitted from Equipment/Tool | Equipment/Tool Usage Details | Equipment/Tool Health |
|---|---|---|---|---|
| User 2 | Tool B (e.g., grinder) | Acoustic Signature Y | e.g., grinding for 1 hour | Noise level (e.g., 85 dB) |

Server 106 may compare/correlate the received acoustic signatures to information in the database (e.g., baseline information). If a high correlation with the stored information in the database is identified, then an event identifying the user, tool type, acoustic pattern, tool usage details, and/or equipment health may be recorded/stored in the database. If the comparison did not identify a high correlation (i.e., a low correlation), portable electronic device 104 may allow a user to store information relating to the tool (e.g., a list of users; an equipment/tool library; acoustic signatures of sounds emitted from various pieces of equipment/tools; equipment/tool usage details; and/or equipment/tool health) in the database of server 106 as a new entry (e.g., the new entry may be used as a baseline for subsequent correlations/queries). That is, portable electronic device 104 may include noise management software (e.g., an app) and may communicate with HPD 102 and server 106 to store, in the database, any new entries, and to create rules/suggestions for operating a tool/equipment based on the correlation.

Portable electronic device 104 may request a user to store a tool/equipment and its related information as a new entry by sending an auditory message to HPD 102. The user can acknowledge the message (and any other message sent to HPD 102) by pressing button 112 or through a voice control (e.g., yes or no when asked/requested by portable electronic device 104). A machine learning algorithm process may ensure that the database improves/grows with data being collected from multiple HPDs 102 on location or that the acoustic signatures are compared against a large acoustic database.

Server 106 may transmit a message to portable electronic device 104 indicating the correlation. Based on the correlation (e.g., a high correlation), portable electronic device 104 may create rules/suggestions and then transmit the rules/suggestions to HPD 102. The rules/suggestions may include appropriate/correct/suggested personal protection equipment ("PPE") needed (e.g., to be worn) and/or a maximum working time in the noisy environment. In certain embodiments, server 106 may also include information which may include suggested PPE equipment and/or suggested time duration for working in the environment for each tool. For example, if an acoustic signature included 100 dB for 2 hours, server 106 may compare/correlate (via an algorithm) this signature to the database (e.g., Table 1), and then relay this correlation to portable electronic device 104. Portable electronic device 104 may then create a rule/suggestion indicating suitable PPE equipment and/or maximum time duration for working with and/or around the specific tool based on comparing/correlating the acoustic signature to information in the database (e.g., an acoustic signature of 100 dB for 2 hours may be correlated to jack hammer 115, and suitable PPE/time duration may be suggested based on this correlation). The rules/suggestions may then be communicated as a message to a user via speakers 109. This correlation may indicate (or be used to determine) if the tool/equipment is being used optimally/correctly, and may be used to identify if the tool/equipment is excessively increasing individual noise exposure. The correlation may also indicate tools/equipment that require maintenance or replacement. The correlation may also indicate a contribution a specific tool/equipment makes to a worker's sound exposure profile, and/or that co-workers in close proximity to the sound are being affected by a tool/equipment. The correlation may also indicate a percentage of noise exposure attributed to each tool/equipment, and/or when the time limit is reached for using that tool/equipment.

As noted above, server 106 may determine if the tool/equipment is working within operational limits (e.g., equipment/tool health) and may send a message to portable electronic device 104 indicating the equipment/tool health. Portable electronic device 104 may then create and send a message to the user via HPD 102 (e.g., replace the equipment because it is too loud; stop using the equipment; send the equipment in for maintenance). Safety/operations personnel may be advised by portable electronic device 104 if noise levels are changing due to the type, frequency, and use patterns of the equipment/tool (e.g., equipment gets louder; equipment being used improperly: operators need further training on equipment use). By knowing the task and tool/equipment to be used, and knowing the normal (correct/proper) noise levels (e.g., acoustic signatures) within a given area, it may be possible to accurately predict the combined noise levels, thereby suggesting appropriate/correct PPE to be worn and/or a maximum working time (e.g., safe operating conditions).

When collecting specific data about the noise levels and sources of that noise, it may be possible to advise each worker regarding the cause of his/her noise exposure and provide guidance on actions (via messages) that could reduce/prevent noise exposure in the future (e.g., limiting the use of equipment/tool; informing the user that the equipment/tool has been recalled for maintenance; informing the user not to work in a noisy area (e.g., due to equipment) during a certain time period.

Devices, systems, and methods of the disclosure may be implemented by an information handling system (e.g., HPD 102, portable electronic device 104, and/or server 106 may each include an information handling system). For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include a transceiver, random access memory ("RAM"), one or more processing resources such as a central processing unit ("CPU") or hardware or software control logic, read-only memory ("ROM"), and/or other types of nonvolatile memory. Additional components of the information handling system may include one or more disk drives, one or more network ports for communication with external devices as well as various input and output (I/O) devices, such as a keyboard, a mouse, and a video display. The information handling system also may include one or more buses operable to transmit communications between the various hardware components.

The information handling system may also include computer-readable media. Computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such as wires, optical fibers, microwaves, radio waves, and other electromagnetic and/or optical carriers; and/or any combination of the foregoing.

Having described various systems and methods, various embodiments can include, but are not limited to:

In a first embodiment, a system may comprise a hearing protection device; a portable electronic device wirelessly coupled to the hearing protection device; and a server wirelessly coupled to the portable electronic device, wherein the hearing protection device is configured to transmit acoustic signatures to the portable electronic device; and wherein the portable electronic device is configured to transmit the acoustic signatures to the server.

A second embodiment may include the system of the first embodiment, wherein the server comprises one or more of the following: a database comprising a list of users, equipment type, an acoustic signature of sound emitted from equipment, duration of equipment use, application of equipment, and equipment health.

A third embodiment may include the system of the first or second embodiment, wherein the hearing protection device comprises a processor, a microphone, and a transceiver.

A fourth embodiment may include the system of any of the preceding embodiments, wherein the portable electronic device is a smart phone.

A fifth embodiment may include the system of any of the preceding embodiments, wherein the server is cloud based.

A sixth embodiment may include the system of any of the preceding embodiments, wherein the server is configured to correlate the acoustic signatures with information in the database.

A seventh embodiment may include the system of any of the preceding embodiments, wherein the portable electronic device is configured to transmit to the hearing protection device a suggestion based on a correlation with the information in the database.

An eighth embodiment may include the system of any of the preceding embodiments, wherein the suggestion comprises personal protection equipment to be worn and/or a maximum working time.

In a ninth embodiment, a method may comprise monitoring environmental sounds with a hearing protection device; transmitting acoustic signatures from the hearing protection device to a portable electronic device; transmitting the acoustic signatures from the portable electronic device to a server; correlating the acoustic signatures with information in a database; transmitting a message from the server to the portable electronic device indicating the correlation; creating a suggestion with the portable electronic device based on the correlation; and transmitting the suggestion from the portable electronic device to the hearing protection device based on the correlation.

A tenth embodiment may include the method of the ninth embodiment, wherein transmitting a suggestion comprises transmitting a message containing personal protection equipment to be worn and/or a maximum working time.

An eleventh embodiment may include the method of the ninth or tenth embodiment, wherein transmitting a suggestion comprises transmitting a message that an equipment requires maintenance or replacement.

A twelfth embodiment may include the method of any of the ninth through eleventh embodiments, wherein transmitting a suggestion comprises transmitting a message advising the worker when the time limit is reached for using a specific equipment in the future.

A thirteenth embodiment may include the method of any of the ninth through twelfth embodiments, wherein correlating the acoustic signatures comprises comparing the acoustic signatures to a list of users, equipment type, an acoustic signature of sound emitted from equipment, duration of equipment use, application of equipment, and/or equipment health.

A fourteenth embodiment may include the method of any one of the ninth through thirteenth embodiments, further comprising transmitting a request from the portable electronic device to the hearing protection device to store, in the database, tool related information.

A fifteenth embodiment may include the method of any one of the ninth through fourteenth embodiments, further comprising storing, in the database, information including users, equipment type, an acoustic signature of sound emitted from equipment, duration of equipment use, application of equipment, and/or equipment health.

In a sixteenth embodiment, a system may comprise a hearing protection device configured to monitor sounds in an industrial environment and transmit acoustic signatures to a portable electronic device; wherein the portable electronic device is configured to transmit the acoustic signatures to a server; wherein the server is configured to correlate the acoustic signatures with information in a database and transmit a message to the portable electronic device indicating the correlation; wherein the portable electronic device is further configured to create and transmit a suggestion to the hearing protection device based on the correlation.

A seventeenth embodiment may include the method of the sixteenth embodiment, wherein the portable electronic device is further configured to indicate equipment health based on the correlation.

An eighteenth embodiment may include the method of the sixteenth or seventeenth embodiment, wherein the suggestion comprises personal protection equipment to be worn and/or a maximum working time.

A nineteenth embodiment may include the method of any one of the sixteenth through eighteenth embodiments, wherein the information comprises a list of users, equipment type, an acoustic signature of sound emitted from equipment, duration of equipment use, application of equipment, and/or equipment health.

A twentieth embodiment may include the method of any one of the sixteenth through nineteenth embodiments, wherein the portable electronic device is a smart phone and the server is cloud based.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system comprising:
   a hearing protection device;
   a portable electronic device wirelessly coupled to the hearing protection device; and
   a server wirelessly coupled to the portable electronic device,
   wherein the hearing protection device comprises a processor, at least one externally facing microphone and a transceiver,
   wherein the at least one externally facing microphone is configured to receive sound generated by at least one equipment,
   wherein the transceiver is configured to transmit acoustic signatures to the portable electronic device, wherein the acoustic signatures correspond to the sound generated by the at least one equipment;
   wherein the portable electronic device is configured to transmit the acoustic signatures to the server, and
   wherein the server is configured to:
      correlate the acoustic signatures with information in a database, and
      transmit a message to the portable electronic device indicating the correlation, and
   wherein the portable electronic device is further configured to:
      generate a suggestion based on the correlation, wherein the suggestion indicates a time duration for each equipment for working in an environment, and
      transmit the generated suggestion to the hearing protection device.

2. The system of claim 1, wherein the server comprises the following: the database comprising a list of users, equipment type, an acoustic signature of sound emitted from equipment, duration of equipment use, application of equipment, and equipment health.

3. The system of claim 1, wherein the portable electronic device is a smart phone.

4. The system of claim 1, wherein the server is cloud based.

5. The system of claim 1, wherein the suggestion comprises personal protection equipment to be worn and a maximum working time.

6. A method comprising:
   monitoring environmental sounds with a hearing protection device;
   transmitting acoustic signatures from the hearing protection device to a portable electronic device,
   wherein the acoustic signatures correspond to the environmental sounds received by at least one externally facing microphone, and
   wherein the environmental sounds are generated by at least one equipment;
   transmitting the acoustic signatures from the portable electronic device to a server;
   correlating the acoustic signatures with information in a database;

transmitting a message from the server to the portable electronic device indicating the correlation;

creating a suggestion with the portable electronic device based on the correlation, wherein the suggestion indicates a time duration for each equipment for working in an environment; and transmitting the suggestion from the portable electronic device to the hearing protection device based on the correlation.

7. The method of claim 6, wherein transmitting the suggestion comprises transmitting a message containing personal protection equipment to be worn and a maximum working time.

8. The method of claim 6, wherein transmitting the suggestion comprises transmitting a message that an equipment requires maintenance or replacement.

9. The method of claim 6, wherein transmitting the suggestion comprises transmitting a message advising a worker when a time limit is reached for using a specific equipment in the future.

10. The method of claim 6, wherein correlating the acoustic signatures comprises comparing the acoustic signatures to one or more of the following: a list of users, equipment type, an acoustic signature of sound emitted from equipment, duration of equipment use, application of equipment, and equipment health.

11. The method of claim 6, further comprising transmitting a request from the portable electronic device to the hearing protection device to store, in the database, tool related information.

12. The method of claim 6, further comprising storing information, in the database, including the following: users, equipment type, an acoustic signature of sound emitted from equipment, duration of equipment use, application of equipment, and equipment health.

13. A system comprising:
a hearing protection device configured to monitor sounds in an industrial environment and transmit acoustic signatures to a portable electronic device;
wherein the hearing protection device comprises a processor, at least one externally facing microphone and a transceiver,
wherein the at least one externally facing microphone is configured to receive sound generated by at least one equipment,
wherein the portable electronic device is configured to transmit the acoustic signatures to a server, wherein the acoustic signatures correspond to the sound generated by the at least one equipment;
wherein the server is configured to:
    correlate the acoustic signatures with information in a database, and
    transmit a message to the portable electronic device indicating the correlation and
wherein the portable electronic device is further configured to:
    create a suggestion based on the correlation, wherein the suggestion indicates a time duration for each equipment for working in an environment, and
    transmit the suggestion to the hearing protection device.

14. The system of claim 13, wherein the portable electronic device is further configured to indicate equipment health based on the correlation.

15. The system of claim 14, wherein the suggestion comprises personal protection equipment to be worn and/or a maximum working time.

16. The system of claim 13, wherein the information comprises a list of users, equipment type, an acoustic signature of sound emitted from equipment, duration of equipment use, application of equipment, and/or equipment health.

17. The system of claim 16, wherein the portable electronic device is a smart phone and the server is cloud based.

* * * * *